(12) United States Patent
 Jablonski

(10) Patent No.: US 10,933,211 B2
(45) Date of Patent: *Mar. 2, 2021

(54) PATIENT INTERFACE DEVICE WITH A FRAME ASSEMBLY HAVING A DOUBLE-Y SUPPORTING STRUCTURE

(71) Applicant: KONINKLIJKE PHILIPS N.V., Eindhoven (NL)

(72) Inventor: Gregory John Jablonski, Butler, PA (US)

(73) Assignee: Koninklijke Philips N.V., Eindhoven (NL)

( * ) Notice: Subject to any disclaimer, the term of this patent is extended or adjusted under 35 U.S.C. 154(b) by 175 days.

This patent is subject to a terminal disclaimer.

(21) Appl. No.: 15/907,324

(22) Filed: Feb. 28, 2018

(65) Prior Publication Data

US 2018/0185600 A1    Jul. 5, 2018

Related U.S. Application Data

(63) Continuation of application No. 13/818,174, filed as application No. PCT/IB2011/053708 on Aug. 24, 2011, now Pat. No. 9,925,349.

(60) Provisional application No. 61/378,103, filed on Aug. 30, 2010.

(51) Int. Cl.
 *A61M 16/06* (2006.01)
 *A61M 16/00* (2006.01)
 *A61M 16/08* (2006.01)

(52) U.S. Cl.
 CPC .... *A61M 16/0683* (2013.01); *A61M 16/0057* (2013.01); *A61M 16/0605* (2014.02); *A61M 16/0666* (2013.01); *A61M 16/0816* (2013.01); *A61M 16/0875* (2013.01)

(58) Field of Classification Search
 CPC .............. A61M 16/06; A61M 16/0605; A61M 16/0666; A61M 16/0683
 See application file for complete search history.

(56) References Cited

U.S. PATENT DOCUMENTS

| | | |
|---|---|---|
| 6,631,718 B1 | 10/2003 | Lovell |
| 7,318,437 B2 | 1/2008 | Gunaratnam |
| 7,618,390 B2 | 11/2009 | Kilbey |
| 8,857,435 B2 | 10/2014 | Matula |
| 9,095,673 B2 | 8/2015 | Barlow |

(Continued)

FOREIGN PATENT DOCUMENTS

| | | |
|---|---|---|
| CN | 101142000 A | 3/2008 |
| EP | 1057494 A2 | 12/2000 |

(Continued)

*Primary Examiner* — Joseph D. Boecker
(74) *Attorney, Agent, or Firm* — Michael W. Haas

(57) ABSTRACT

A patient interface device is includes a cushion and a frame assembly coupled to the cushion, the frame assembly including a main frame member and a stiffening structure coupled to the main frame member, the stiffening structure having a main arm, a first Y-portion coupled to a first end of the main arm having first and second front branches extending at upward and downward angles, respectively, from the first end of the main arm, and a second Y-portion coupled to a second end of the main arm having first and second rear branches extending at upward and downward angles, respectively, from the second end of the main arm.

16 Claims, 16 Drawing Sheets

(56) References Cited

U.S. PATENT DOCUMENTS

| | | | |
|---|---|---|---|
| 9,597,474 B2* | 3/2017 | Jablonski | A61M 16/0605 |
| 9,925,349 B2* | 3/2018 | Jablonski | A61M 16/0683 |
| 10,213,570 B2* | 2/2019 | Jablonski | A61M 16/06 |
| 2004/0112377 A1 | 6/2004 | Amarasinghe | |
| 2004/0221850 A1 | 11/2004 | Ging | |
| 2004/0226566 A1 | 11/2004 | Gunaratanam | |
| 2005/0150499 A1 | 7/2005 | Bordewick | |
| 2006/0060200 A1 | 3/2006 | Ho | |
| 2006/0237017 A1 | 10/2006 | Davidson | |
| 2009/0044808 A1* | 2/2009 | Guney | A61M 16/0666 128/206.24 |
| 2009/0107508 A1* | 4/2009 | Brambilla | A61M 16/0683 128/207.11 |
| 2009/0173349 A1 | 7/2009 | Hernandez | |
| 2009/0183739 A1 | 7/2009 | Wondka | |
| 2009/0241961 A1* | 10/2009 | McAuley | A61M 16/161 128/205.25 |
| 2010/0000534 A1 | 1/2010 | Kooij | |
| 2010/0229868 A1* | 9/2010 | Rummery | A61M 16/06 128/205.25 |
| 2010/0258136 A1* | 10/2010 | Doherty | A61M 16/0683 128/207.17 |
| 2010/0307502 A1* | 12/2010 | Rummery | A61M 16/0622 128/205.25 |
| 2010/0313891 A1* | 12/2010 | Veliss | A61M 16/0622 128/206.26 |
| 2010/0319700 A1* | 12/2010 | Ng | A61M 16/0057 128/206.28 |
| 2011/0265796 A1 | 11/2011 | Amarasinghe | |
| 2011/0308520 A1* | 12/2011 | McAuley | A61M 16/0825 128/203.26 |
| 2012/0017912 A1 | 1/2012 | Ging | |
| 2013/0074845 A1 | 3/2013 | Smith | |
| 2015/0246200 A1* | 9/2015 | Neff, Jr. | A61M 16/0816 128/202.27 |
| 2018/0140796 A1* | 5/2018 | Haibach | A61M 16/0622 |

FOREIGN PATENT DOCUMENTS

| | | |
|---|---|---|
| EP | 2022528 A2 | 2/2009 |
| WO | WO0205883 A1 | 1/2002 |
| WO | WO2006044120 A2 | 4/2006 |
| WO | WO2008106716 A1 | 9/2008 |
| WO | WO2009052560 A1 | 4/2009 |

* cited by examiner

Section V-V

Section U-U

Section T-T

Section S-S

Section R-R

Section Q-Q

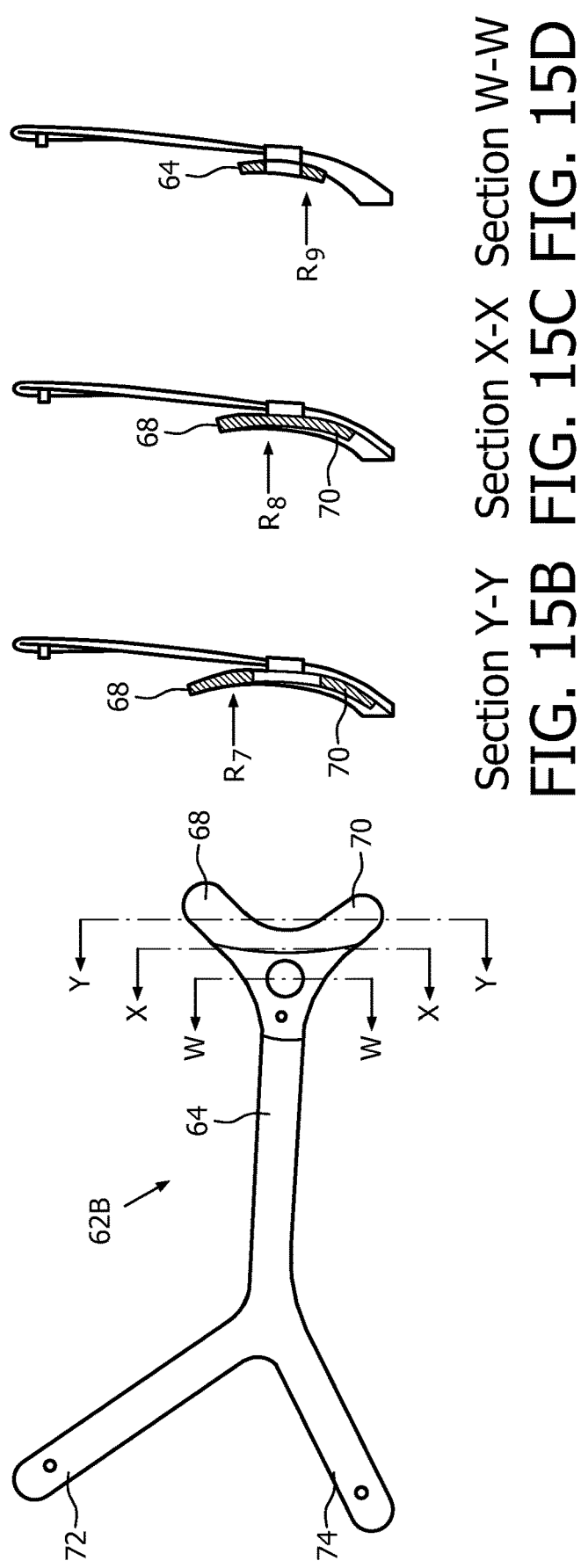

Section Z-Z

PATIENT INTERFACE DEVICE WITH A FRAME ASSEMBLY HAVING A DOUBLE-Y SUPPORTING STRUCTURE

CROSS-REFERENCE TO RELATED APPLICATIONS

This patent application is a Continuation of U.S. patent application Ser. No. 13/818,174, filed Feb. 21, 2013, which claims the priority benefit under 35 U.S.C. § 371 of international patent application no. PCT/IB2011/053708, filed Aug. 24, 2011, which claims the priority benefit under 35 U.S.C. § 119(e) of U.S. Provisional Application No. 61/378,103 filed on Aug. 30, 2010, the contents of which are herein incorporated by reference.

BACKGROUND OF THE INVENTION

1. Field of the Invention

The present invention relates to patient interface devices for transporting a gas to and/or from an airway of a user, and in particular, to a patient interface device having a frame assembly that includes a supporting structure having a double-Y configuration.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, which varies with the patient's respiratory cycle, to treat a medical disorder, such as sleep apnea syndrome, in particular, obstructive sleep apnea (OSA), or congestive heart failure.

Non-invasive ventilation and pressure support therapies involve the placement of a patient interface device including a mask component on the face of a patient. The mask component may be, without limitation, a nasal mask that covers the patient's nose, a nasal cushion having nasal prongs that are received within the patient's nares, a nasal/oral mask that covers the nose and mouth, or a full face mask that covers the patient's face. The patient interface device interfaces the ventilator or pressure support device with the airway of the patient, so that a flow of breathing gas can be delivered from the pressure/flow generating device to the airway of the patient. It is known to maintain such devices on the face of a wearer by a headgear having one or more straps adapted to fit over/around the patient's head.

Patients that that require pressure support therapy are often confronted with the problem of finding a suitable patient interface device. In finding a suitable patient interface device, such patients frequently struggle with issues relating to the seal and stability of the patient interface device, the comfort of the patient interface device, the size/weight of the patient interface device, and the sizing of the patient interface device. These challenges, if not addressed properly, can compromise the patient's compliance with the prescribed therapy.

More specifically, during the night, the stability of a mask seal will be challenged by the patient moving about in his or her bed. The changing head position can lead to air delivery hose torque and general interference with other objects (e.g. pillows, sheets, blankets, etc.). Thus, stability, and consequently seal, is a challenge for any patient interface device in the market.

In addition, patient comfort is an important factor, and can be negatively impacted in many ways. For example, over-tightening of the headgear (to compensate for lack of seal and stability) can increase pressure on the face and head, which in turn can result in pressure points and/or skin breakdown. Other components of the patient interface device (e.g. straps, frames, headgear, etc.) can also add discomfort for the patient because the geometry of such components can conflict with facial structures.

Furthermore, the general weight of the patient interface device can negatively impact a patient's experience by causing additional facial pressure or compounding over-tightening issues. Patient interface device weight can also negatively affect the seal and stability. Certain patients also have problems with a patient interface device interfering with his or her line of sight, and overall patient interface device size has been known to cause claustrophobia is some patients.

Finally, properly sizing a patient interface device can be difficult because facial structures vary greatly among patients. Not all patient interface devices are able to accommodate this range of differences, thus requiring either more sizes/variations or not providing an optimal fit for the majority of the user population.

SUMMARY OF THE INVENTION

Accordingly, it is an object of the present invention to provide a patient interface device that overcomes the shortcomings of conventional patient interface device. This object is achieved according to one embodiment of the present invention by providing a patient interface device that includes a cushion and a frame assembly coupled to the cushion, the frame assembly including a main frame member and a stiffening structure coupled to the main frame member, the stiffening structure having a main arm, a first Y-portion coupled to a first end of the main arm having first and second front branches extending at upward and downward angles, respectively, from the first end of the main arm, and a second Y-portion coupled to a second end of the main arm having first and second rear branches extending at upward and downward angles, respectively, from the second end of the main arm.

In another embodiment, a frame assembly for a patient interface device is provided that includes a main frame member and a stiffening structure coupled to the main frame member, the stiffening structure having a main arm, a first Y-portion coupled to a first end of the main arm having first and second front branches extending at upward and downward angles, respectively, from the first end of the main arm, and a second Y-portion coupled to a second end of the main arm having first and second rear branches extending at upward and downward angles, respectively, from the second end of the main arm.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIG. 15A is a side elevational view of the stiffening structure of the frame assembly of FIGS. 11-12 having lines which indicate certain cross-sectional views thereof shown in FIGS. 15B-15D;

DETAILED DESCRIPTION OF THE EXEMPLARY EMBODIMENTS

Figure 1:
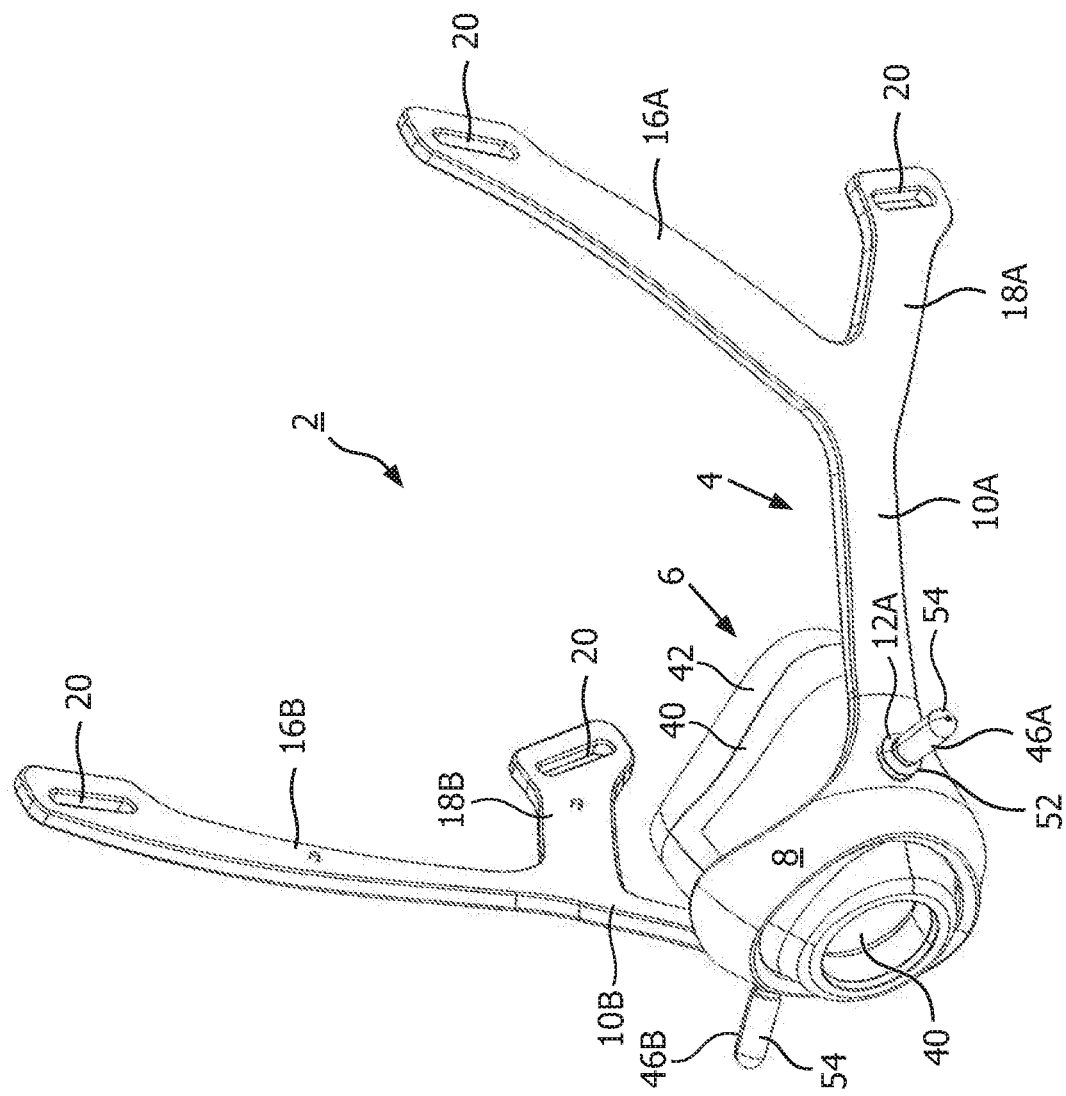
FIG. 1 is a front perspective view of a patient interface device according to an exemplary embodiment of the present invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 9:
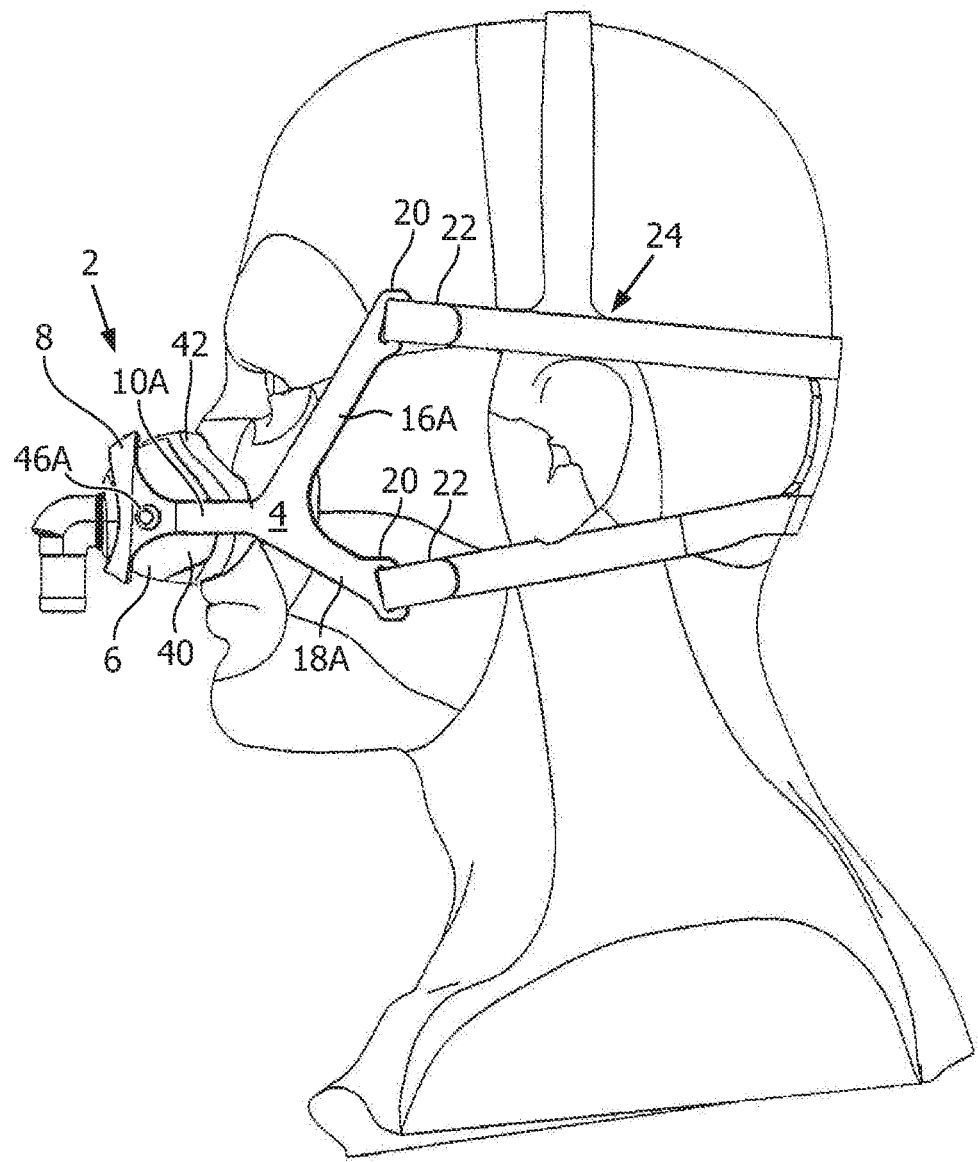
FIG. 9 is a side view and FIG. 10 is an perspective view showing the patient interface device of FIG. 1 attached to a patient.
Figure 10:
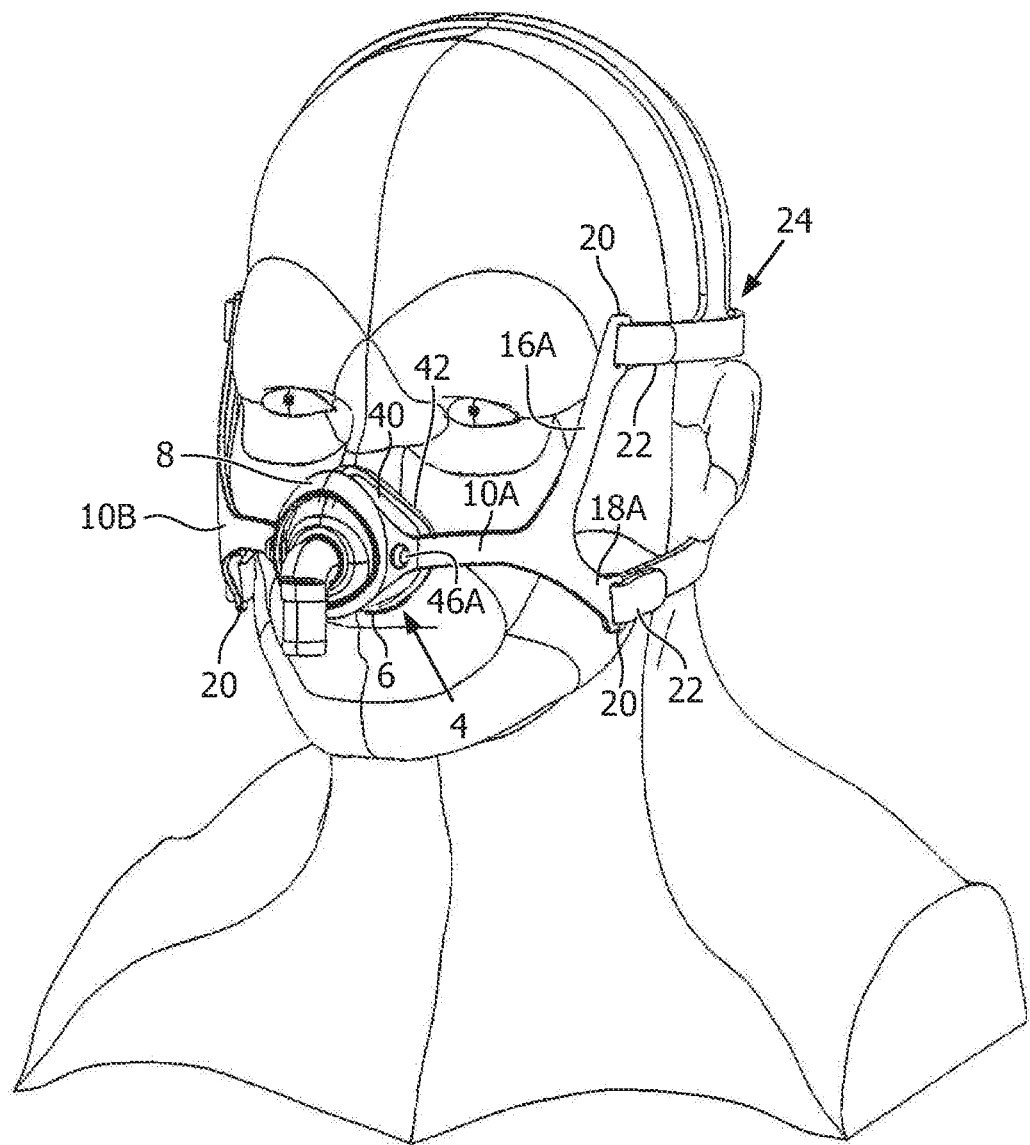

FIG. 1 is a front perspective view of a patient interface device 2 according to an exemplary embodiment of the present invention. FIG. 9 is a side view and FIG. 10 is a front perspective view showing patient interface device 2 attached to a patient. Patient interface device 2 includes a frame member 4 and a cushion 6 coupled to frame member 4, each of which is described in greater detail herein.

Figure 2:
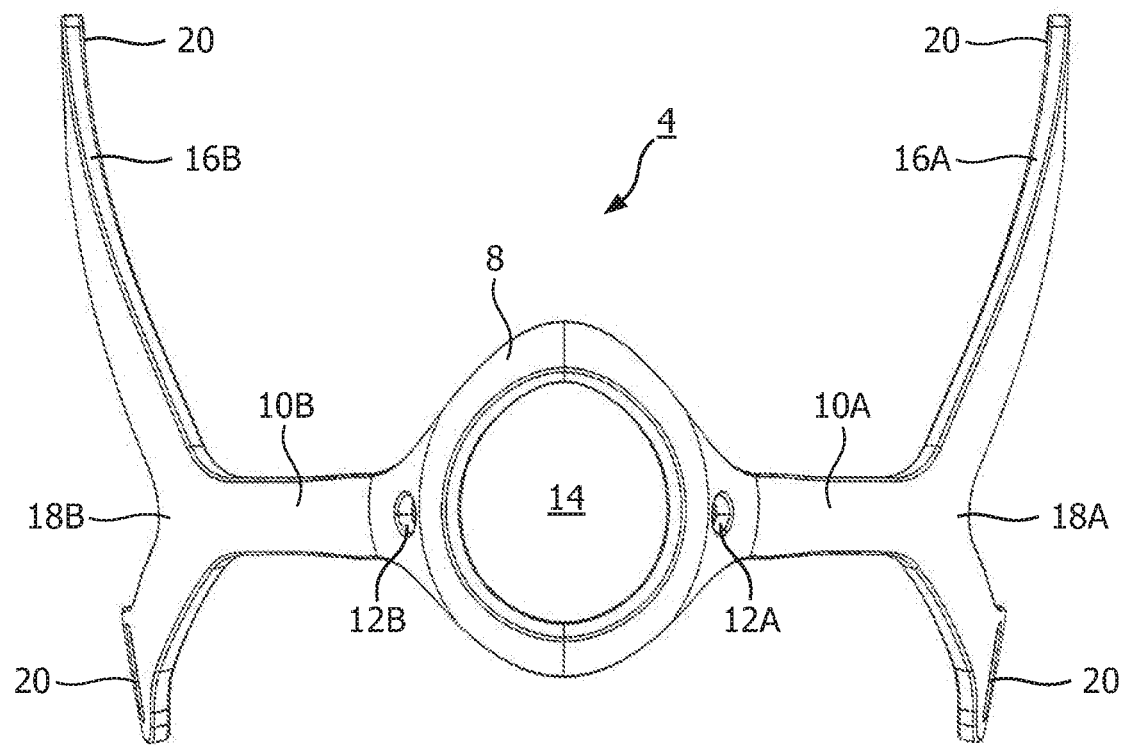
FIGS. 2, 3, 4 and 5 are front, rear, top and side elevational views, respectively, of a frame member of the patient interface device of FIG. 1.
Figure 3:
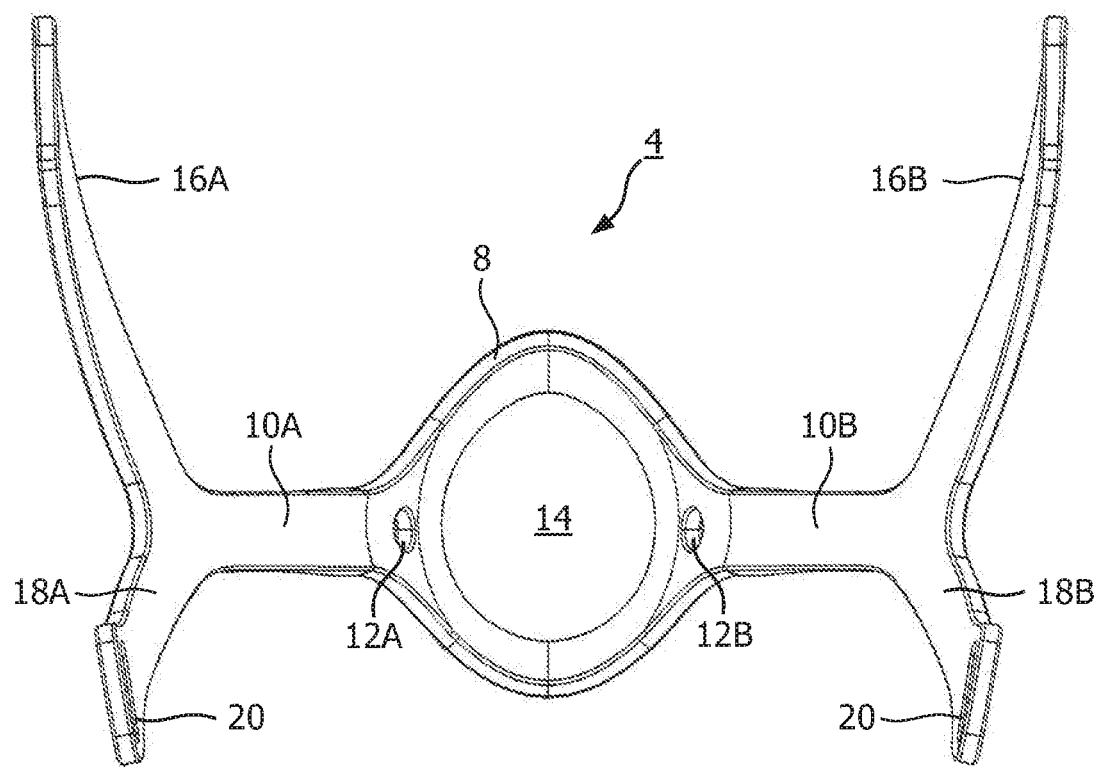
Figure 4:
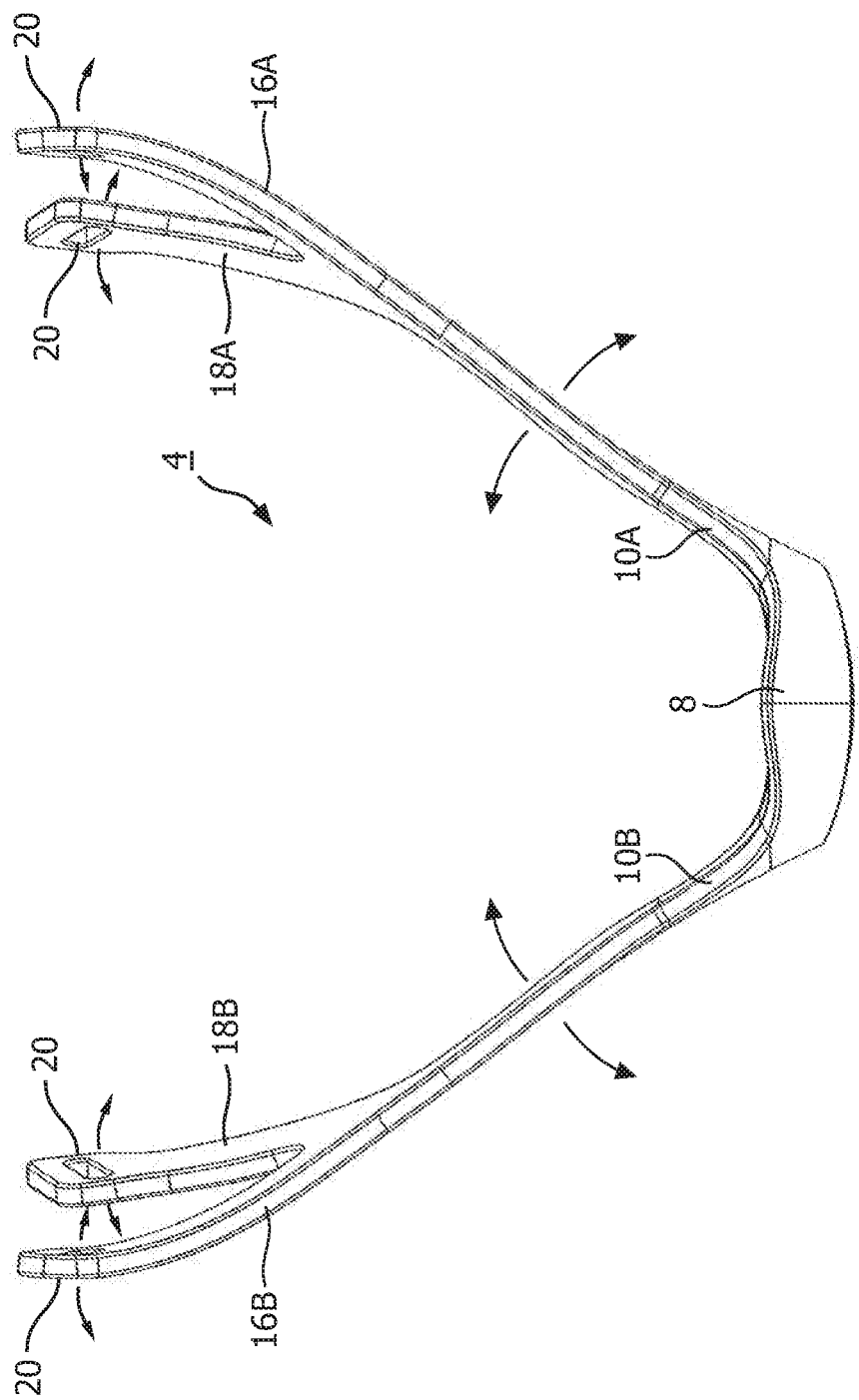
Figure 5:
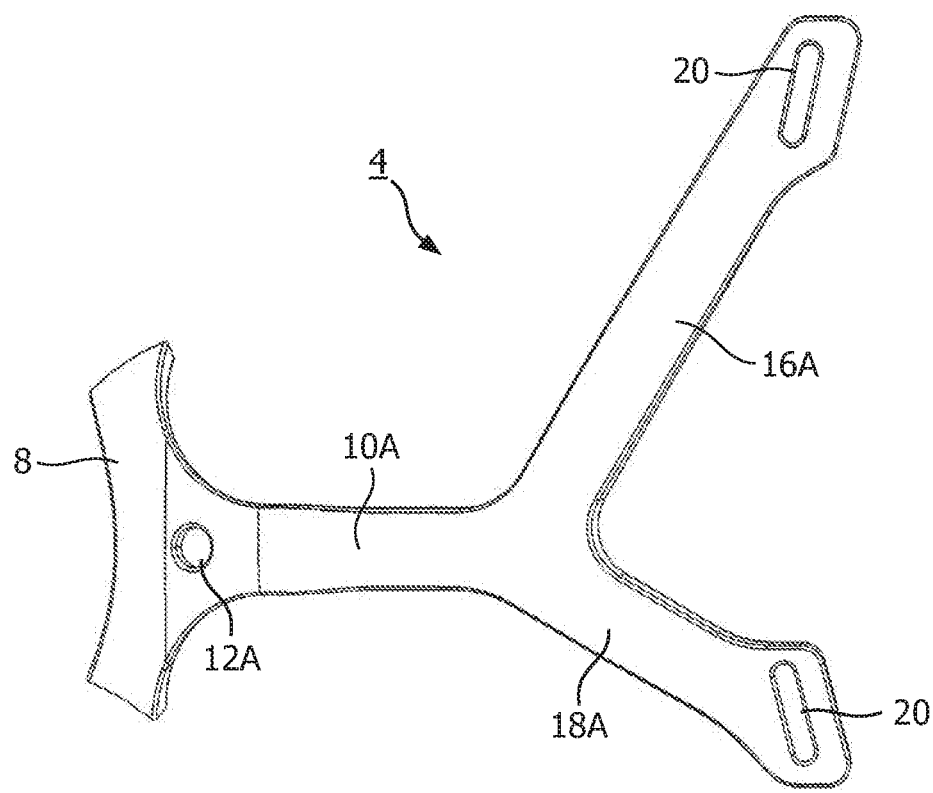

FIGS. 2, 3, 4, and 5 are front, rear, top and side elevational views, respectively, of frame member 4 of patient interface device 2. Frame member 4 includes a generally annular central member 8 having first and second main arms 10A, 10B extending outwardly from opposites sides thereof. Main arm 10A includes orifice 12A extending therethrough, and main arm 10B includes orifice 12B extending therethrough. In the exemplary embodiment, orifices 12A, 12B are positioned at a location on main arms 10A, 10B adjacent central member 8. The purpose of orifices 12A, 12B is described in detail elsewhere herein. In addition, as seen in FIGS. 2 and 3, central member 8 defines central orifice 14.

Frame member 4 further includes a first branching member 16A extending upwardly at an angle from main arm 10A and a first branching member 16B extending upwardly at an angle from main arm 10B. In one particular, non-limiting embodiment, first branching members 16A, 16B extend upwardly from the respective main arm 10A, 10B at an angle of about 60 degrees, although other angles are also possible. Furthermore, frame member 4 also includes a second branching member 18A extending downwardly at an angle from main arm 10A and a second branching member 18B extending downwardly at an angle from main arm 10B. In one particular, non-limiting embodiment, second branching members 18A, 18B extend downwardly from the respective main arm 10A, 10B at an angle of about 30 degrees], although other angles are also possible. Also in one particular, non-limiting embodiment, main arms 10A and 10B extend for about 55-60 mm from the center of orifices 12A, 12B to the inner angles formed between the branching members 16A and 18A and 16B and 18B, respectively.

Moreover, as seen in FIGS. 1-5, the distal end of each of first branching member 16A, 16B and second branching member 18A, 18B includes a respective loop member 20 for receiving a respective strap 22 of headgear assembly 24 (FIGS. 9 and 10). In the exemplary embodiment, frame member 4 is made of a thermoplastic or thermoset material.

Figure 6:
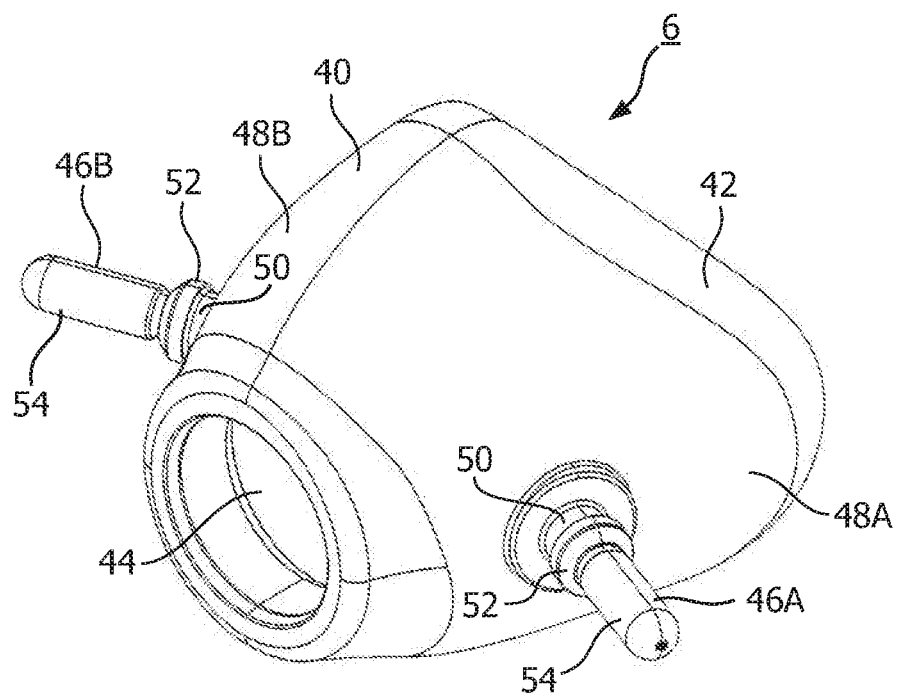
FIGS. 6, 7 and 8 are front perspective, front elevational and rear elevational views, respectively, of the cushion of the patient interface device of FIG. 1.
Figure 7:
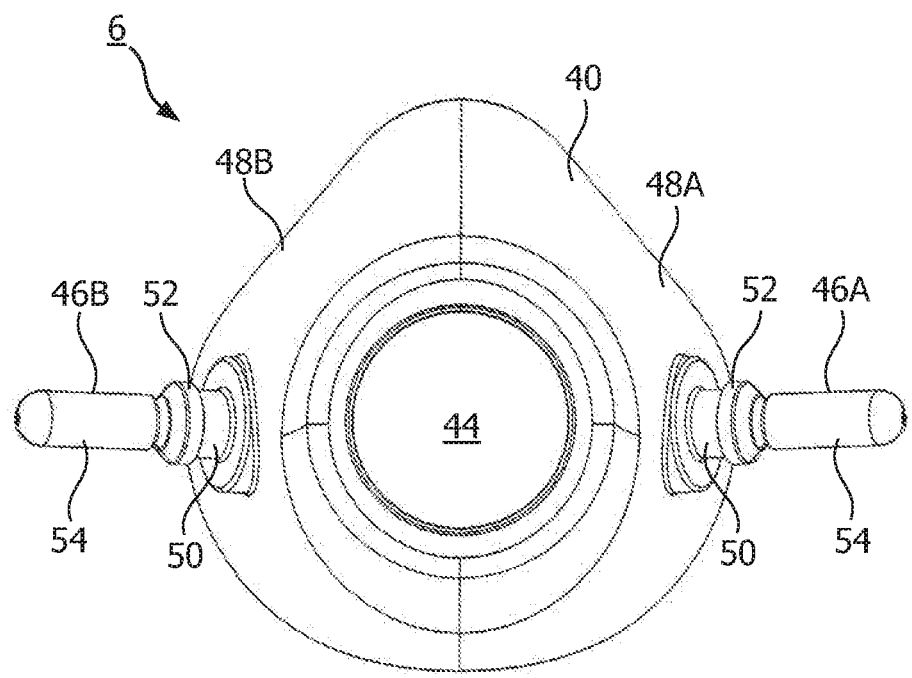
Figure 8:
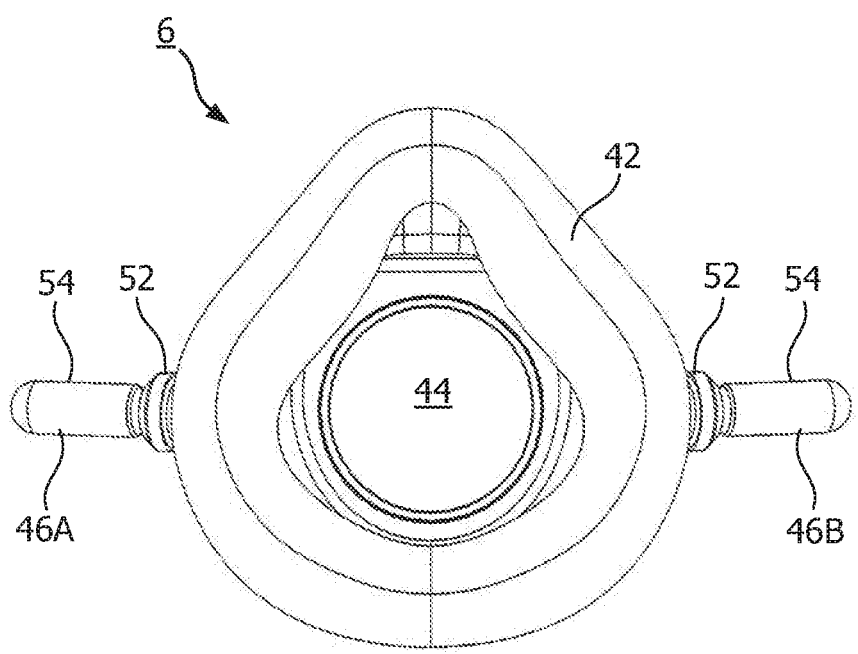

FIGS. 6, 7, and 8 are front perspective, front elevational and rear elevational views, respectively, of cushion 6 of patient interface device 2. In the exemplary embodiment, cushion 6 is defined from a unitary piece of soft, flexible, cushiony, elastomeric material, such as, without limitation, silicone, an appropriately soft thermoplastic elastomer, a closed cell foam, or any combination of such materials. Cushion 6 includes a main body portion 40 having a sealing portion 42 coupled to a first end thereof. Sealing portion 42 is structured to form a seal against a face of the patient. In the illustrated embodiment, cushion 6 is in the form of a nasal mask. However, other types of patient sealing assemblies, such as a nasal/oral mask, nasal cannula, or a nasal cushion, which facilitate the delivery of the flow of breathing gas to the airway of a patient, may be substituted for cushion 6 while remaining within the scope of the present invention.

In addition, main body portion 40 defines orifice 44 at the second end thereof opposite the first end. Orifice 44 is structured to enable cushion 6 to be fluidly coupled to a fluid connector such as an elbow conduit, which in turn is fluidly coupled a pressure generating device such as a ventilator or a CPAP machine through a gas delivery hose.

Cushion 6 further includes generally cylindrically shaped posts 46A and 46B extending from first and second sides 48A and 48B, respectively, of main body 40. Each post 46A, 46B is positioned about midway between the first and send end of cushion 6. In addition, each post 46A, 46B includes inner cylindrical portion 50, enlarged portion 52, and outer cylindrical portion 54.

When patient interface device 2 is assembled, the second end of main body 40 is inserted through central orifice 14 defined by central member 8. In addition, post 46A is inserted through orifice 12A and post 46B is inserted through orifice 12B. More specifically, as seen in FIG. 1, in each case, outer cylindrical portion 54 and enlarged portion 52 are inserted through the respective orifice 12A, 12B such that each enlarged portion 52 rests against the outer surface of main arm 10A, 10B and prevents outer cylindrical portion 54 from sliding back through orifice 12A, 12B. In addition, each inner cylindrical portion 50 is able to turn within the respective orifice 12A, 12B.

The branching nature of the sides of frame member 4, giving it a "T" or "Y" shape, allows for flexing of frame member 4 in certain directions while at the same time limiting flexing in other directions. In particular, main arms 10A, 10B are able to flex in the directions shown by the arrows in FIG. 4 (i.e., parallel to the top and bottom surface of main arms 10A, 10B), but are not able to freely flex in a direction transverse to the longitudinal axis thereof (i.e., perpendicular to the top and bottom surface of main arms 10A, 10B). In addition, each of the first branching members 16A, 16B and second branching member 18A, 18B are able to flex independently of one another in the directions shown by the arrows in FIG. 4 (i.e., parallel to the top and bottom surface of the branching members), but are not able to freely flex in a direction transverse to the longitudinal axis thereof (i.e., perpendicular to the top and bottom surface of the branching members). This controlled flexing addresses several issues present in the prior art relating to seal, stability and comfort discussed elsewhere herein, as it passively accommodates for many facial and head geometries to allow for optimal fit and comfort. The branched structure of frame member 4 also increases the stability of patient interface device 2 through patient movement and hose torque, which provides an optimal seal for the patient.

In addition, the selection of the material for frame member 4 in conjunction with the geometry of frame member 4 as described herein allows for flexing to accommodate the vast variation in patient facial structures and head dimensions. In the exemplary embodiment, the material will be soft enough to provide for flexing in the desired directions as described herein, but rigid enough to limit the flexing in non-desired directions as described herein. Also, the geometry will, in the exemplary embodiment, allow for accommodation of not only the temple, cheek and jaw regions, but will also cover varying head sizes and nose locations. The geometry of portions of frame member 4 may, for example, vary in thickness, existence of ribs or other structures, and/or general dimensioning to accommodate differences in flexing due to the material properties, but will maintain the branching shape described herein.

Other alternative methods of controlling the direction of flexing of frame ember 4 in the various directions can be accomplished with the use of structures such as hinges incorporated therein. The hinge can be accomplished in a number of different ways, such as with mechanical interlocking (removable or permanent) or overmolding with materials such as silicone or other elastomers.

Furthermore, the branching nature of the sides of frame member 4, giving it the "T" or "Y" shape discussed above, moves the mounting or anchor point (i.e., loops 20) for patient interface device 2 on the head of the patient through headgear assembly 24 further back along the side of the head. Typical mounting locations of nasal masks have been on one or many of the following: cheeks, forehead, and chin. By moving the mounting point away from the front of the face, it improves the issues with claustrophobia and line of sight infringement. It also limits the pressure and potential discomfort from over-tightening to the less sensitive areas of the face.

In addition, the interaction between posts 46A, 46B and orifices 12A, 12B provide the connection point for cushion 6 to frame 4. That connection point provides for a passive auto-adjustment mechanism for cushion 6, as posts 46A and 46B, and thus cushion 6, are able to rotate relative to frame member 4. In the exemplary embodiment, each post 46A, 46B has enough interference with frame member 4 to limit excessive rotation but not enough resistance to prevent auto-adjustment. Also in the exemplary embodiment, the cylindrical shape of each post 46A, 46B, as opposed to an oval or other geometry, allows for an infinite amount of positions instead of discrete positioning. This auto-adjusting feature optimizes the angle of engagement of cushion 6 to the face of the patient and increases the chance for an optimal seal across many patient faces of differing sizes and shapes. It also decreases the chance of undue pressure along the sealing portion 42 of cushion 6 on the face (particularly the upper lip) of the patient. Lastly, this auto-adjusting feature provides the ability of cushion 6 to adjust during patient movement, thus increasing stability throughout the night.

Thus, the combination of the flexing frame member 4 and the auto-adjusting cushion 6 allows for placement of frame member 4 on the face to vary in order to meet the individual patient's needs. This allows an opportunity for the patient to alleviate any possible pressure points and/or optimize seal and stability. In addition, the mounting point of cushion 6 to frame member 4 has been moved closer to the patient's face, which increases the stability of patient interface device 2 by moving the fulcrum closer to the patient's face (moment arm decreases). It also lessens the overall profile of patient interface device 2, creating a lower profile that improves overall size and appearance.

Figure 11:
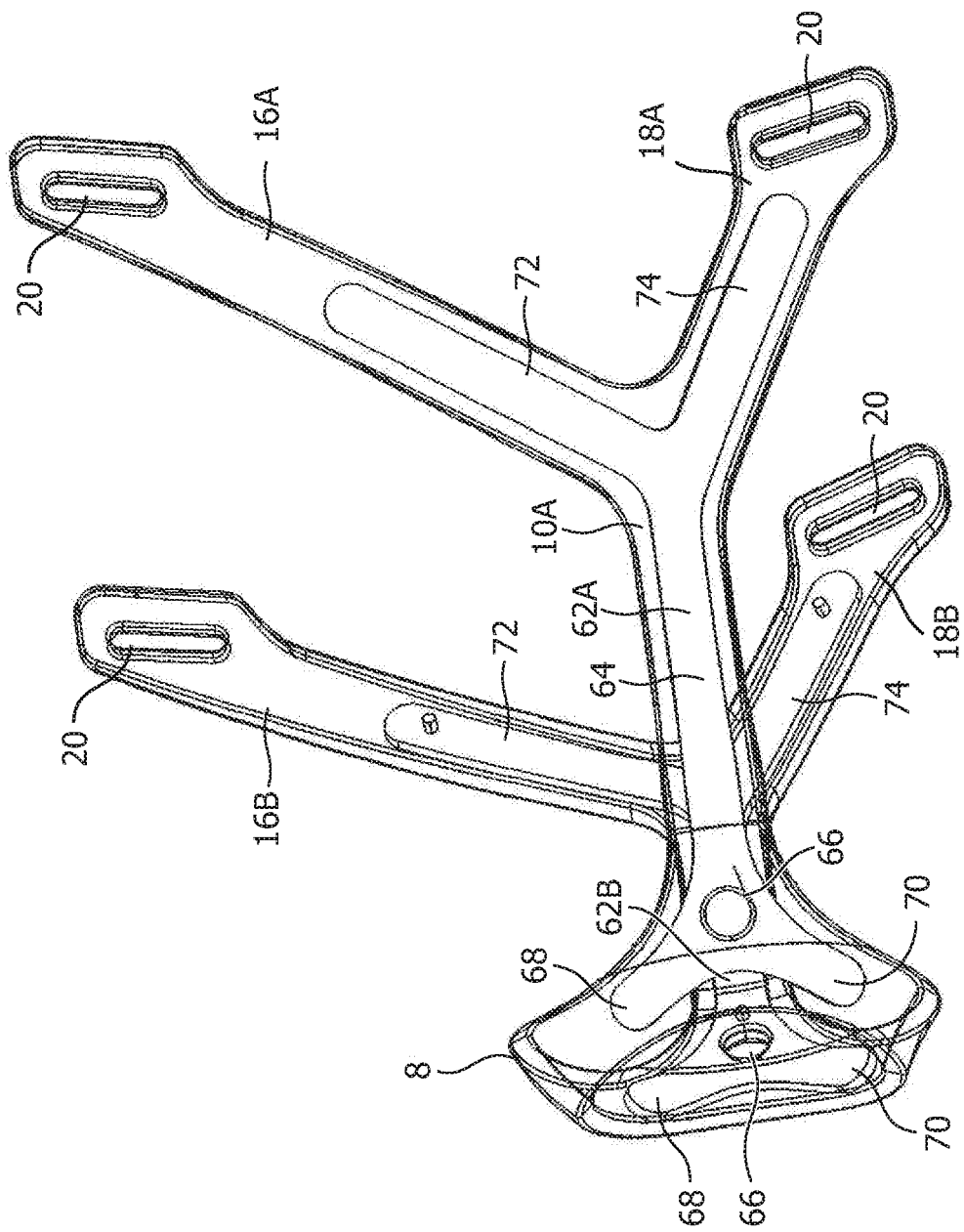
FIGS. 11 and 12 perspective and side schematic diagrams of a frame assembly according to an alternative exemplary embodiment of the invention.
Figure 12:
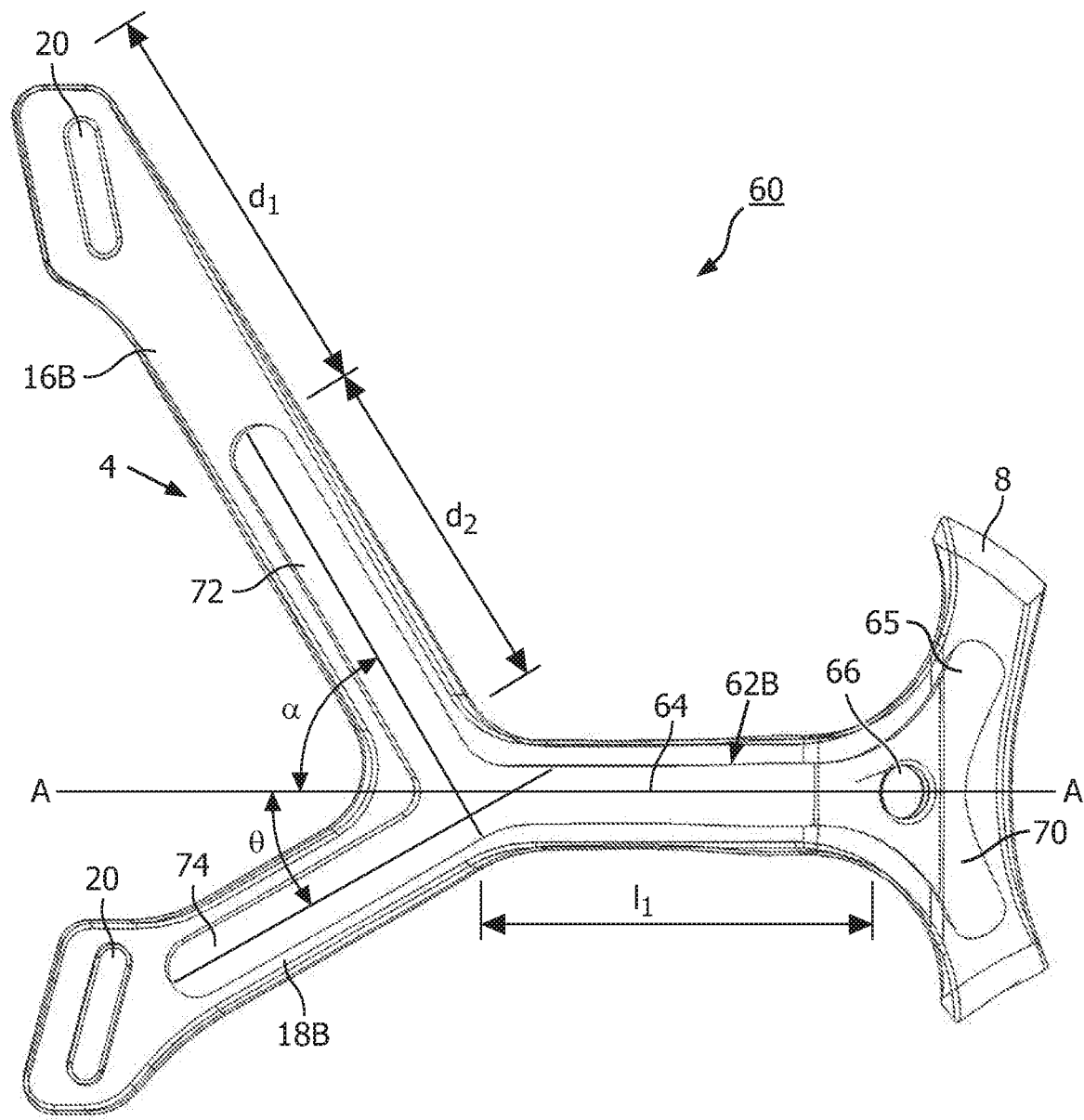

An alternative exemplary embodiment of the invention is shown in FIGS. 11 and 12, and includes frame assembly 60 which may be coupled to cushion 6 as described elsewhere herein or another suitable cushion, such as, without limitation, a known or hereafter developed nasal/oral mask, nasal cushion, pillows style cushion or full face mask. Frame assembly 60 includes a frame member 4 as described elsewhere herein having inserts provided therein or attached (e.g., bonded) thereto (i.e., to the exterior surface) in the form of right and left stiffening structures 62A and 62B. In the exemplary, non-limiting embodiment, frame member 4 is made of a high durometer silicone, such as, without limitation, 75 Shore A (±5 Shore A) durometer LSR (liquid silicone rubber), overmolded onto right and left stiffening structures 62A and 62B as shown in FIGS. 11 and 12. Also in the exemplary embodiment, stiffening structures 62A and 62B are made of a thermoplastic material such as a polycarbonate like HP4, although other materials, such as polypropylene, may also be used. In addition, frame assembly 60 could have a fabric covering or other surface treatment or texturing for aesthetics, patient comfort, or for the wicking of moisture or patient-caused heat.

Figure 13:
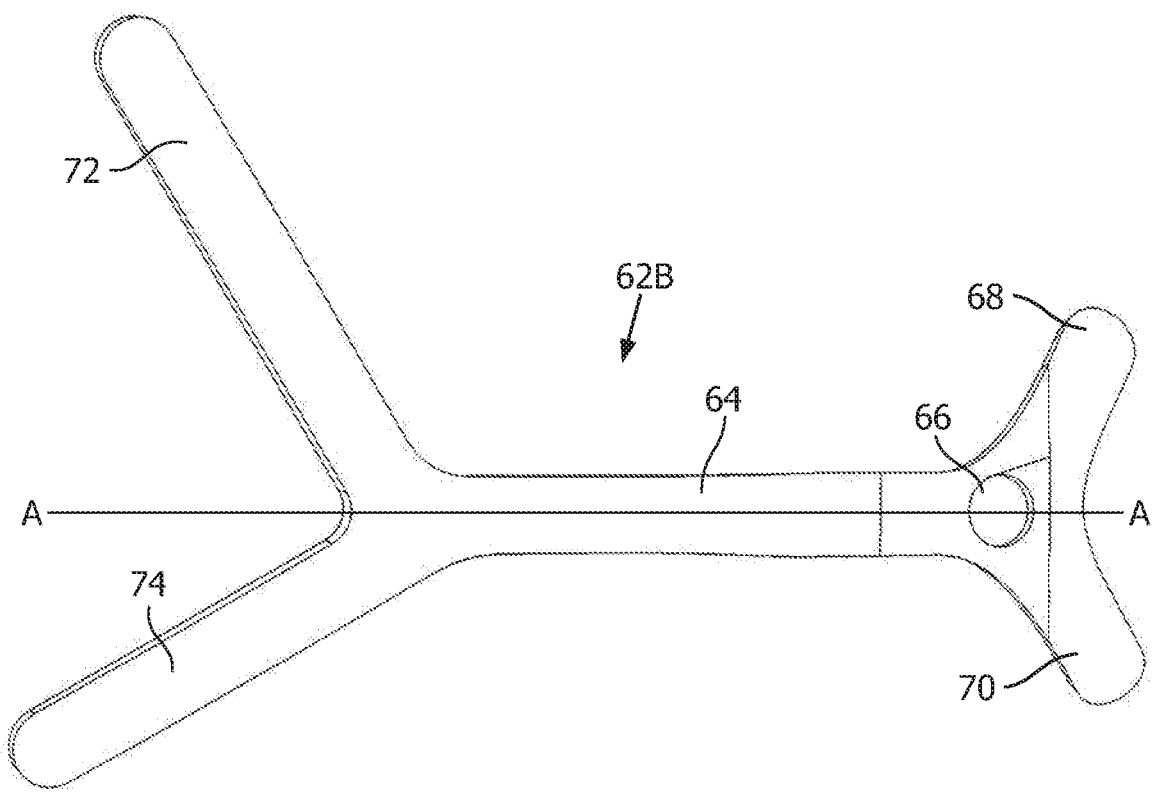
FIG. 13 is a side elevational view of an internal support structure of the frame assembly shown in FIGS. 11 and 12.

FIG. 13 is a side elevational view of left stiffening structure 62B. Right stiffening structure 62A is identical in structure and symmetrical to left stiffening structure 62B. Stiffening structures 62A and 62B each have a generally double-Y shaped footprint, wherein one of the Y portions faces the patient's ear while the other of the Y portions faces the cushion attached to frame assembly 60 (which, as discussed elsewhere herein, could be a nasal cushion, a nasal/oral mask, a pillows cushion or a full face cushion). In particular, stiffening structures 62A and 62B each include main arm 64 having orifice 66, front branches 68 and 70 extending at upward and downward angles, respectively, from main arm 64, and rear branches 72 and 74 extending at upward and downward angles, respectively, from main arm 64.

In the exemplary embodiment, main body 64, front branches 68 and 70, and rear branches 72 and 74 each have a thickness of about 0.058 inches and a width of about 0.25 inches. Also in the exemplary embodiment, main arms 10A, 10B and branching members 16A, 16B, 18A, 18B have a thickness of about 0.125 inches and a width of about 0.475 inches. The purpose of stiffening structures 62A and 62B is to provide vertical support and stabilize cushion 6 and preserve the patient seal while forces are exerted thereon as a result of patient movement (e.g., hose related forces). The mask-side-Y (front branches 68 and 70) has a generally symmetric shape with respect to line AA shown in FIGS. 12 and 13, while the ear-side-Y (rear branches 72 and 74) is asymmetric with respect to line AA shown in FIGS. 12 and 13.

In one particular embodiment, the portion of each stiffening structure 62A, 62B between each Y has a length (labelled as $l_1$ in FIG. 12) of 55-60 mm. This size is key in positioning the ear-side-Y such that the headgear connections and force vectors are away from the immediate region of the cushion and yet negotiate around the ear region for the majority of the patient population. The ear-side-Y has an upper member (rear branch 72) that has a centerline that positioned at an angle $\alpha$ with respect to the line AA of FIG. 12 (the centerline of main arm 64). In the illustrated embodiment, $\alpha$ is roughly 60 degrees. The ear-side-lower member (rear branch 74) has a centerline that positioned at an angle $\theta$ with respect to the line AA of FIG. 12. In the illustrated embodiment, $\theta$ is roughly 30 degrees. In addition, in the illustrated embodiment, the upper member of the ear-side-Y (rear branch 72) extends along half of associated first branching member 16A, 16B such that $d_1=d_2$ as shown in FIG. 12. The lower member of the ear-side-Y (rear branch 72) extends roughly the length of the associated first branching member 18A, 18B (up to a point adjacent to where loop member 20 begins).

Figure 14A:
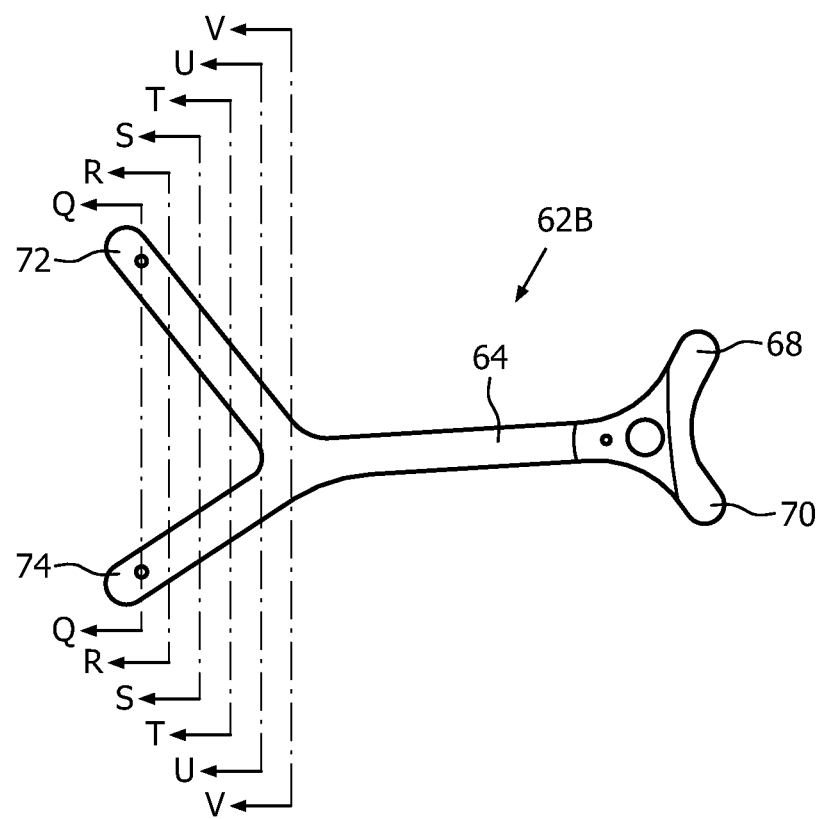
FIG. 14A is a side elevational view of the stiffening structure of the frame assembly of FIGS. 11-12 having lines which indicate certain cross-sectional views thereof shown in FIGS. 14B-14G.
Figure 14B:
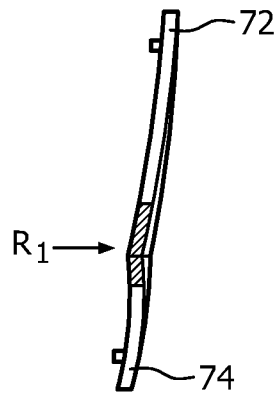
Figure 14C:
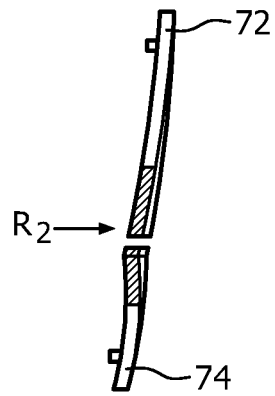
Figure 14D:
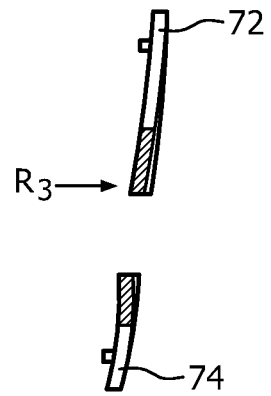
Figure 14E:
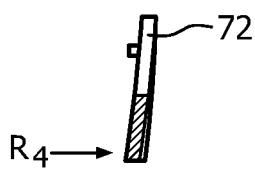
Figure 14F:
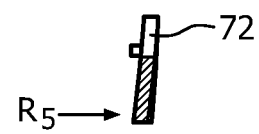
Figure 14G:
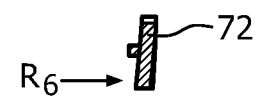

FIG. 14A is a side elevational view of stiffening structure 62B having lines which indicate certain cross-sectional views of stiffening structure 62B shown in FIGS. 14B-14G. Referring to FIGS. 14A-14G, in the exemplary embodiment, the degree of cross-sectional curvature (with reference to the longitudinal axis of main arm 64) of the ear-side-Y (i.e., of both rear branch 72 and rear breach 74) decreases from the first end of the ear-side-Y immediately adjacent to the end of main arm 64 to the distal end of the ear-side-Y (i.e., the distal end of both rear branch 72 and rear breach 74). In particular, as shown in FIGS. 14B-14G, that decreasing curvature is prescribed by the ear-side-Y having a succession of cross-sectional radii $R_1$ through $R_6$ that increase from the first end of the ear-side-Y to the distal end of the ear-side-Y ($R_1<R_2<R_3<R_4<R_5<R_6$). This curvature is designed to match the contours of the human face for the majority of the patient population. In one particular embodiment, $R_1=116.85$ mm, $R_2=132.59$ mm, $R_3=159.51$ mm, $R_4=223.23$ mm, $R_5=247.66$ mm, and $R_6=421.98$ mm.

FIG. 15A is a side elevational view of stiffening structure 62B having lines which indicate certain cross-sectional views of stiffening structure 62B shown in FIGS. 15B-15D. Referring to FIGS. 15A-15D, in the exemplary embodiment, the degree of cross-sectional curvature (with reference to the longitudinal axis of main arm 64) of the mask-side-Y (i.e., of both front branches 68 and 70) increases from the first end of the mask-side-Y immediately adjacent to the end of main arm 64 to the distal end of the mask-side-Y (i.e., the distal end of both front branch 68 and front breach 70). In particular, as shown in FIGS. 15B-15D, that increasing curvature is prescribed by the mask-side-Y having a succession of cross-sectional radii $R_7$ through $R_9$ that decrease from the first end of the ear-side-Y to the distal end of the ear-side-Y ($R_7>R_8>R_9$). In one particular embodiment, $R_7=32.59$ mm, $R_8=32.31$ mm, and $R_3=30.44$ mm.

Figure 16A:
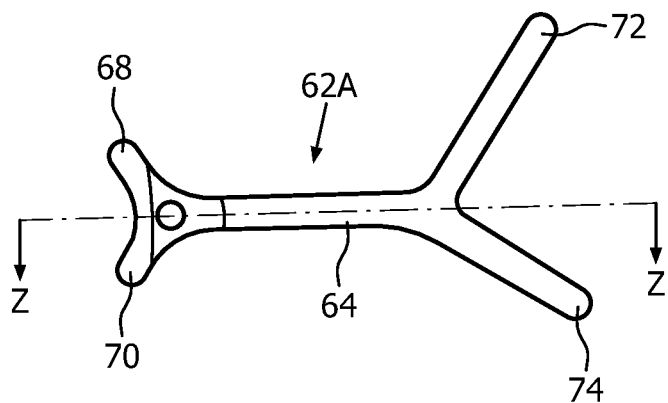
FIG. 16A is a side elevational view of the stiffening structure of the frame assembly of FIGS. 11-12.
Figure 16B:
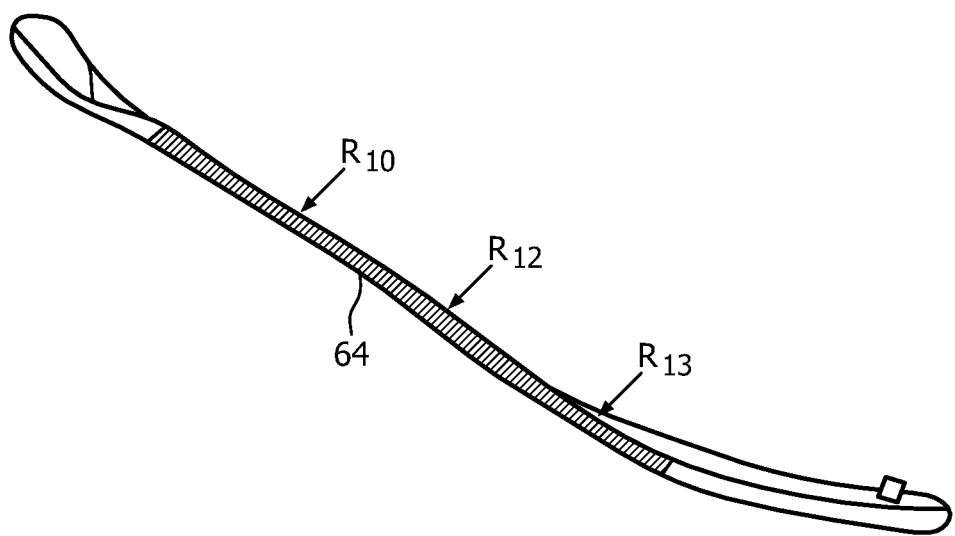
FIG. 16B is a cross sectional view of the stiffening structure of the frame assembly of FIGS. 11-12 taken along lines Z-Z of FIG. 16A.

FIG. 16A is a side elevational view of stiffening structure 62A, and FIG. 16B is a cross sectional view of stiffening structure 62A taken along lines Z-Z of FIG. 16A. As seen in FIG. 16B, main arm 64 has a curvature that is prescribed by radii $R_{10}$, $R_{11}$ and $R_{12}$. In one particular embodiment, $R_{10}=181.07$ mm, $R_{11}=1520.95$ mm, and $R_{12}=121.46$ mm.

Figure 17:
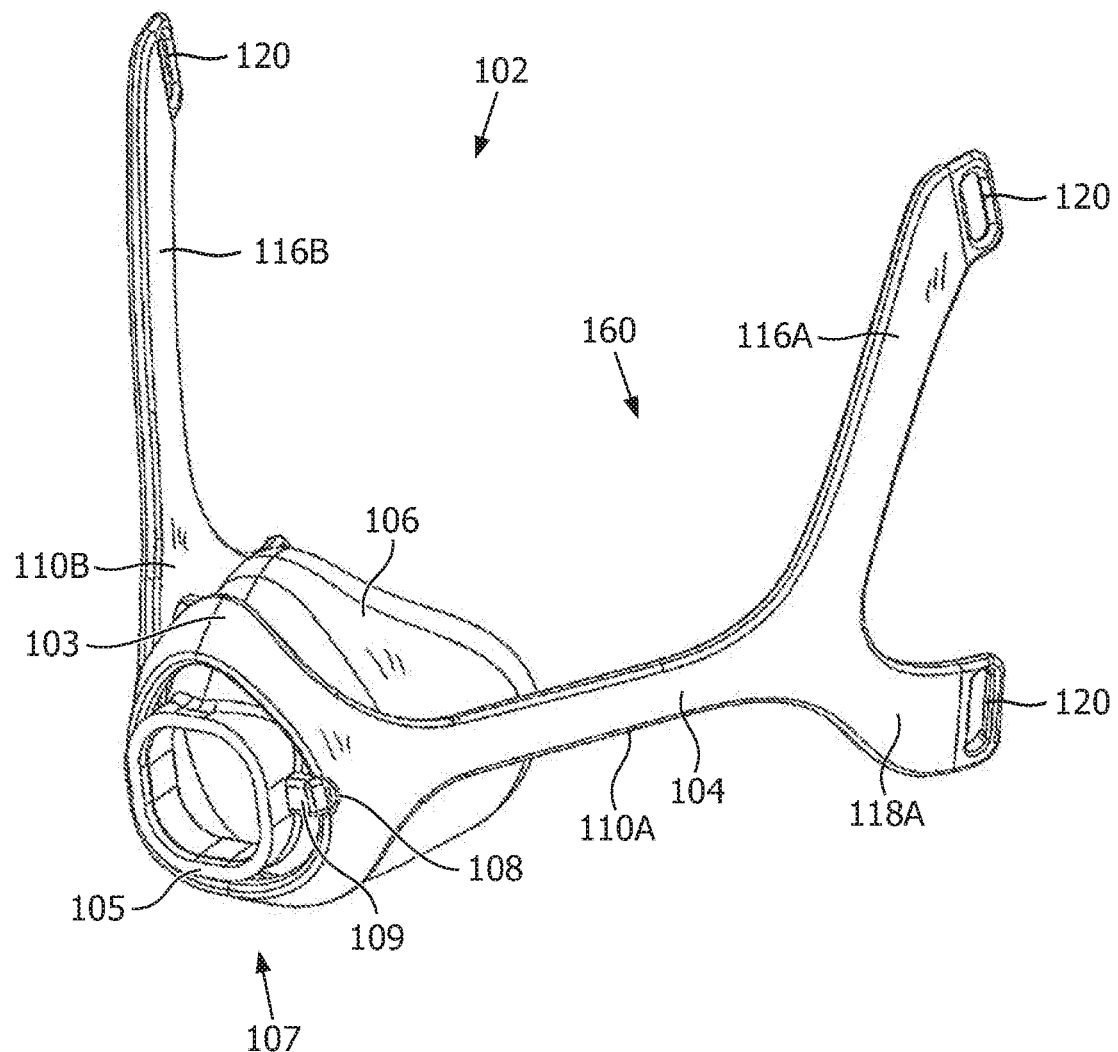
FIG. 17 is a front perspective view of a patient interface device according to a further embodiment of the present invention.
Figure 18:
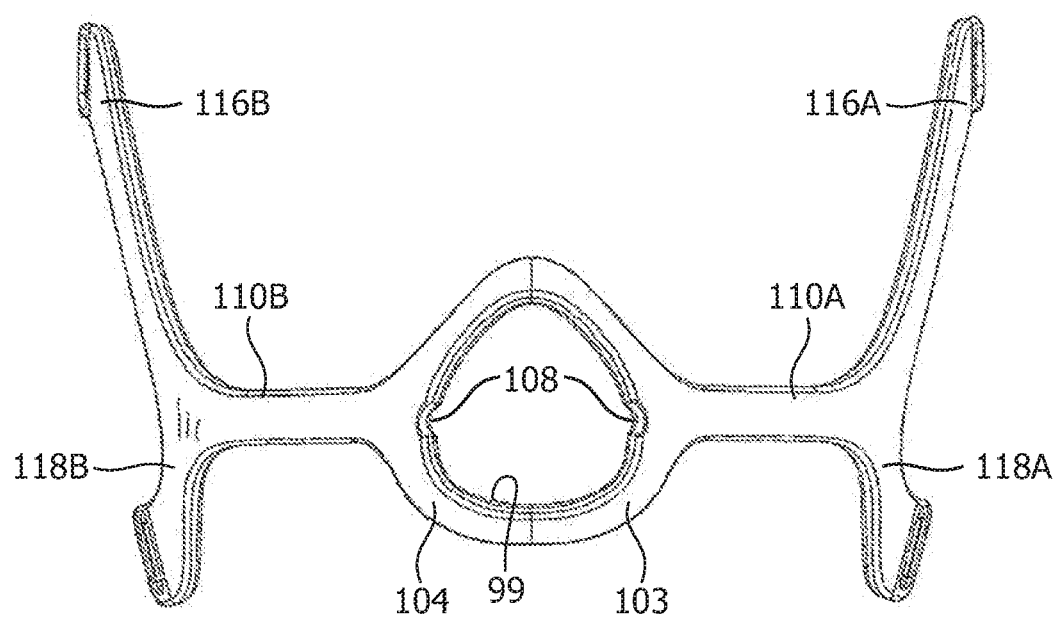
FIGS. 18 and 19 are front and side view, respectively, of a frame member of the patient interface device of FIG. 17.
Figure 19:
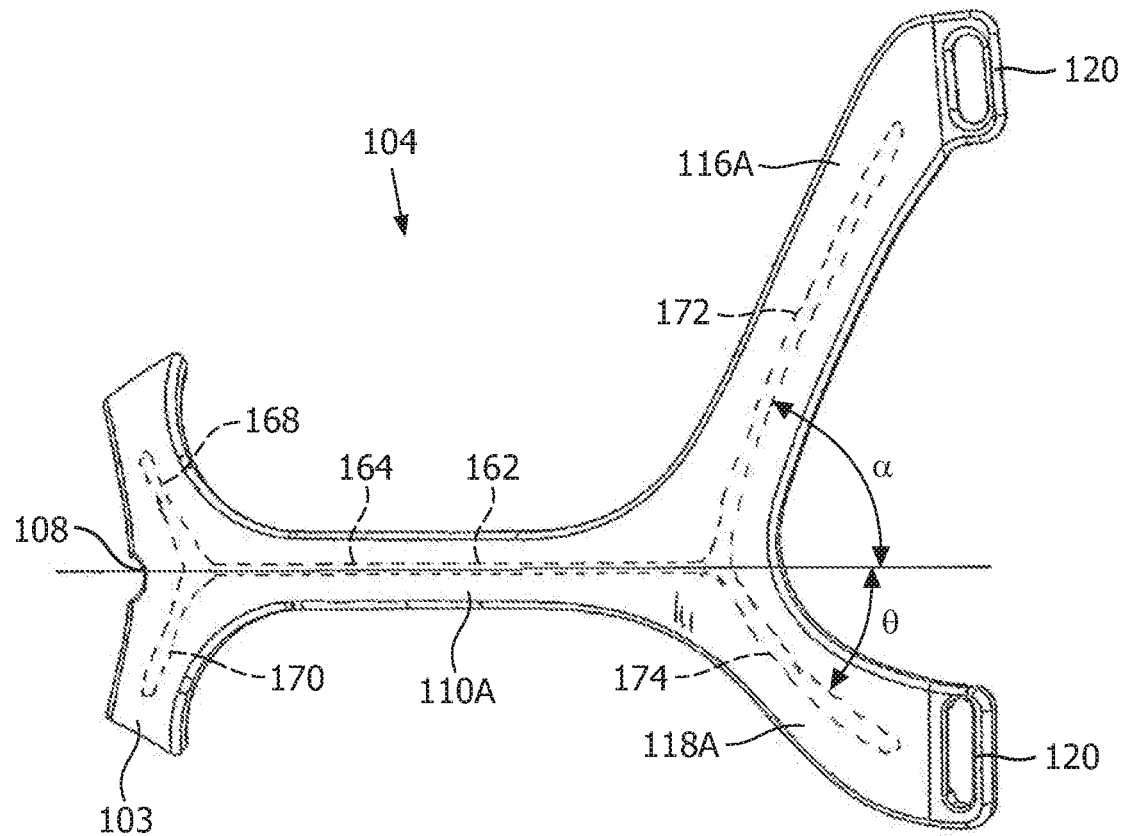

FIG. 17 is a front perspective view of a patient interface device 102 according to a further embodiment of the present invention, and FIGS. 18 and 19, are front and side view, respectively, of a frame member 104 of the patient interface device of FIG. 17. Patient interface device 102 is generally similar to patient interface device 2 describe above with some of the differences being discussed in detail below. As in the previous embodiment, a cushion 106 is attached to a frame assembly 160 that includes a frame member 104 such that the cushion is moveable relative to the frame member.

Frame member 104 includes a generally annular central member 103 having first and second main arms 110A and 110B. An opening 99 is defined in central member 103. Frame member 104 includes a first branching member 116A extending upwardly at an angle from main arm 110A and a first branching member 116B extending upwardly at an angle from main arm 110B. In one particular, non-limiting embodiment, first branching members 116A, 116B extend upwardly from the respective main arm 110A, 110B at an angle of about 63 degrees±5 degrees, although other angles are also possible. Note that branching members 116A, 116B are more curved or have a more arcuate shape than the branching members of the previous embodiments. This curbed shape is believed to provide a frame that more close conforms to the anatomy of a human head.

Furthermore, frame member 104 also includes a second branching member 118A extending downwardly at an angle from main arm 110A and a second branching member 118B extending downwardly at an angle from main arm 110B. In one particular, non-limiting embodiment, second branching members 118A, 118B extend downwardly from the respective main arm 110A, 110B at an angle of about 44 degrees 5 degrees, although other angles are also possible. Note that branching members 118A, 118B are more curved or have a more arcuate shape than the branching members of the previous embodiments. This curbed shape is believed to provide a frame that more close conforms to the anatomy of a human head. The distal end of each of first branching member 116A, 116B and second branching member 118A, 118B includes a respective loop member 120 for receiving a respective strap of headgear assembly 24.

In this embodiment, the coupling of cushion 106 to the frame member is accomplished via a coupling assembly 107 that includes a pair of protrusions 109 provided on each side of a collar 105 coupled to cushion 106. In the illustrated embodiment, at least a portion of each protrusion 109 is seated or disposed in a slot or groove 108 that is provided in frame member 104. This arrangement allows cushion 106 to move relative to frame member 104 by, for example, pivoting about an axis defined through protrusions 109. Such movement allows the cushion to automatically seat itself on the patient when the patient interface device is donned by the user.

In the exemplary embodiment, each main arm 110A and 110B of frame member 104 is defined by a stiffening member 162 disposed in a flexible material. In an exemplary embodiment, the stiffening member is defined by a plastic and the flexible material is a compressed foam covered in fabric. Stiffening structures 162 each include a main arm 164, front branches 168 and 170 extending at upward and downward angles, respectively, from main arm 164, and rear branches 172 and 174 extending at upward and downward angles, respectively, from main arm 164. In the exemplary embodiment, angle $\alpha=63+5$ degrees and angle $\theta=44+5$ degrees. Front branches 168 and 170 and rear branches 172 and 174 are generally longer than in previous embodiments and are also less wide.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface device, comprising:
   a cushion member having a central opening;
   a patient circuit adapted to be coupled to the cushion member at the central opening;
   a frame member coupled to the cushion; and
   a headgear assembly adapted to be selectively coupled to the frame member, wherein the frame member includes:
      a central member coupled to the cushion and having a generally arcuate shape adapted to span a portion of the cushion generally proximate to the central opening,
      a first arm member having a first axis, a first end coupled to a first end of the central member, and a second end, wherein the first arm member extends from the first end of the central member,
      a second arm member having a second axis, a first end coupled to a second end of the central member, and a second end, wherein the second arm member extends from the second end of the central member,
      a first branch member having a first branch member axis, a first end coupled to the second end of the first arm member, and a second end,
      a second branch member having a second branch member axis, a first end also coupled to the second end of the first arm member, and a second end,
      a third branch member having a third branch member axis, a first end coupled to the second end of the second arm member, and a second end,
      a fourth branch member having a fourth branch member axis, a first end also coupled to the second end of the second arm member, and a second end,
   wherein the central member, the first arm member, the second arm member, the first branch member, the second branch member, the third branch member, and the fourth branch member are generally strap-like structures,
   wherein the headgear assembly is coupled to the second end of the first branch member, the second end of the second branch member, the second end of the third branch member, and the second end of the fourth branch member,
   wherein the first arm member spans at least a portion of a first side of a user's face and the second arm member spans at least a portion of a second side of the user's face opposite the first side of the user's face responsive to the patient interface assembly being donned by the user,
   wherein the first branch member and the third branch member are positioned above the user's ears responsive to the patient interface assembly being donned by the user,
   wherein the second branch member and the fourth branch member are positioned below the user's ears responsive to the patient interface assembly being donned by the user,
   wherein the second end of the first branch member and the second end of the second branch member are aligned with respect to and positioned along a first vertical axis spanning from a top portion of the first side of the user's face to a bottom portion of the first side of the user's face responsive to the patient interface assembly being donned by the user, the first vertical axis being perpendicular to the first axis of the first arm, and
   wherein the second end of the third branch member and the second end of the fourth branch member are aligned with respect to and positioned along a second vertical axis spanning from a top portion of the second side of the user's face to a bottom portion of the first side of the user's face responsive to the patient interface assembly being donned by the user, the second vertical axis being perpendicular to the second axis of the second arm.

2. The patient interface device according to claim 1, wherein the central member, the first arm member, the second arm member, the first branch member, the second branch member, the third branch member, and the fourth branch member are formed as a unitary structure.

3. The patient interface device according to claim 2, further comprising:
   a first portion of a generally soft material coupled to the first arm member, the first branch member, and the second branch member; and
   a second portion of the generally soft material coupled to the second arm member the third branch member, and the fourth branch member.

4. The patient interface device according to claim 1, wherein the first arm member and the second arm member each has a length between 55 and 60 mm.

5. The patient interface device according to claim 1, wherein the first axis of the first arm member and second axis of the second arm member are generally disposed in common plane responsive to the patient interface assembly being donned by the user.

6. The patient interface device according to claim 1, wherein the first axis of the first arm member and the first branch member axis are disposed at an angle α relatively to one another, wherein the second axis of the second arm member and the third branch member axis are also disposed an angle α relative to one another, and wherein angle α has a range of 58-68 degrees.

7. The patient interface device according to claim 1, wherein the first axis of the first arm member and the first branch member axis are disposed at an angle α relatively to one another, wherein the second axis of the second arm member and the third branch member axis are also disposed an angle α relative to one another, and wherein angle α is approximately 60 degrees.

8. The patient interface device according to claim 1, wherein the first axis of the first arm member and the second branch member axis are disposed at an angle θ relatively to one another, wherein the second axis of the second arm member and the fourth branch member axis are also disposed an angle θ relative to one another, and wherein angle θ has a range of 39-49 degrees.

9. The patient interface device according to claim 1, wherein the first axis of the first arm member and the second branch member axis are disposed at an angle θ relatively to one another, wherein the second axis of the second arm member and the fourth branch member axis are also disposed an angle θ relative to one another, and wherein angle θ is approximately 30 degrees.

10. The patient interface device according to claim 1, wherein the first branch member has a first length and the second branch member has a second length, wherein the first length is greater than the second length.

11. The patient interface device according to claim 1, wherein the first branch member and the third branch member each has a first length, wherein the second branch member and the fourth branch member each has a second length, wherein the first length is greater than the second length.

12. The patient interface device according to claim 1, wherein the patient circuit includes an elbow member that has a bend proximate to the central opening.

13. The patient interface device according to claim 1, wherein the first branch member includes a first slot defined in the second end of the first branch member, wherein the third branch member includes a second slot defined in the second end of the third branch member, and wherein the first slot and the second slot are sized and configured to receive a strap portion of the headgear assembly.

14. The patient interface device according to claim 1,
wherein the first arm member, the first branch member, and the second branch member comprise a first stiffening member and a first portion of a flexible material operatively coupled to the first stiffening member, the first portion of the flexible material being disposed between the first stiffening member and a first portion of the user, and
wherein the second arm member, the third branch member, and the fourth branch member comprise a second stiffening member and a second portion of the flexible material operatively coupled to the second stiffening member, the second portion of the flexible material being disposed between the stiffening member and a second portion of the user.

15. The patient interface device according to claim 14, wherein the stiffening member is formed from plastic.

16. The patient interface device according to claim 14, wherein the flexible material includes foam, silicone, or fabric.

\* \* \* \* \*